United States Patent [19]
Omurtag et al.

[11] Patent Number: 6,132,437
[45] Date of Patent: Oct. 17, 2000

[54] METHOD AND STEREOTACTIC APPARATUS FOR LOCATING INTRACRANIAL TARGETS GUIDING SURGICAL INSTRUMENTS

[76] Inventors: Ahmet Omurtag, 523 W. 112 Apt. 42, New York, N.Y. 10025; Oğuz Cataltepe, 534 E. 88th St. Apt #1F, New York, N.Y. 10128

[21] Appl. No.: 09/353,225

[22] Filed: Jul. 14, 1999

[51] Int. Cl.⁷ .................................................. A61B 19/00
[52] U.S. Cl. ........................... 606/130; 600/417; 600/429
[58] Field of Search ................................. 606/130, 129, 606/1, 108; 600/417, 429; 33/511

[56] References Cited

U.S. PATENT DOCUMENTS

| | | | |
|---|---|---|---|
| 5,176,689 | 1/1993 | Hardy et al. | 606/130 |
| 5,207,688 | 5/1993 | Carol | 606/130 |
| 5,618,288 | 4/1997 | Calvo | 606/130 |
| 5,695,501 | 12/1997 | Carol et al. | 606/130 |
| 5,891,157 | 4/1999 | Day et al. | 606/130 |
| 5,971,997 | 10/1999 | Guthrie et al. | 606/130 |
| 5,984,930 | 11/1999 | Maciunas et al. | 606/130 |

*Primary Examiner*—Pedro Philogene

[57] ABSTRACT

A method and an instrument are presented for reliably, accurately and easily locating intracranial targets and guiding surgical instruments to intracranial targets in human patients. An adjustment apparatus and a portable guider 70 constitute main components of the invention. The method and instrument make use of images of natural reference points or fiducial markers found in CT/MRI images of patient's head. In accordance with the present method, after the adjustment apparatus is mechanically adjusted based on the information gathered from CT/MRI images, the adjustments are transferred by a special procedure to the portable guider. The portable guider is the only component employed during surgery, resulting in minimal general intrusion with the work of the surgeon.

2 Claims, 15 Drawing Sheets

METHOD AND STEREOTACTIC APPARATUS FOR LOCATING INTRACRANIAL TARGETS GUIDING SURGICAL INSTRUMENTS

BACKGROUND—FIELD OF THE INVENTION

This invention relates to stereotactic devices and localization methods used in neurosurgical operations in human patients. It more particularly relates to a method which utilizes CT/MRI based anatomical reference points or fiducial markers to localize a defined entry and target point and proper trajectory in three-dimensional space. It also specifically relates to a guidance system and instrument holder to hold and to guide ventricular catheters as well as other needed surgical instruments in a precise orientation until the instrument tip is placed into the intracranial target point.

BACKGROUND—DESCRIPTION OF PRIOR ART

The neurosurgeons frequently deal with deep-seated intracerebral lesions or targets. The difficulty arises from localization of these surgical targets. Even if brain surface is exposed during surgery, deep-seated lesions or target will stay unexposed to surgeon. Therefore, numerous methods and stereotactic devices from free hand technique alone to highly sophisticated devices were defined, developed and used in neurosurgery to localize an unexposed intracranial target. Some of these methods and devices have excellent suitability for some surgical interventions but not so for some others. The neurosurgeon's needs for a stereotactic device to localize and to reach an unexposed intracranial targets might differ from case to case. He/she may need a very sophisticated and very precise image guided devices in some cases such as resection of a deep seated brain tumors or may need a very simple mechanical guide in some cases such as ventricular catheter placement or may prefer to use free hand technique without any assistance of a device. Therefore, the neurosurgeon will choose the best suited instrument for his/her specific surgical intervention based upon the device's capabilities and limitations for that specific intervention. We will review prior art specifically for these instruments and associated procedures.

Ventricular catheter placement, intracranial pressure (ICP) monitoring electrode placement, drainage of intracerebral collections such as hematoma, abscess, and tumor biopsy through small skull openings are widely performed neurosurgical procedures. Four ventricles of the human brain are interconnected cerebrospinal fluid (CSF) filled cavities. Application of ventricular catheter placement includes ICP monitoring, external drainage of CSF, ventriculo-peritoneal (VP)/ventriculo-atial VA shunting procedures and the instillation of pharmacologic therapeutic agents. Ventricular catheter is a simple, thin silastic tube with small holes at the tip. Ventricular catheter placement is generally performed by introducing a premeasured catheter through a small opening on skull (burr hole) and brain tissue and placing the tip of the catheter into one of the lateral ventricles of the brain with free hand technique.

Neurosurgeon uses some external anatomical landmarks, such as nasion, coronal suture and occipital protuberence for spatial orientation during placement. A wide variety of strategies and visual aiming techniques have been described based on these external landmarks to define a proper entry point and trajectory (Pang D. et al., *J.Neurosurg.* 80:750–755(1994), Flamm E. S. et al., *J. Neurosurg.* 25:67–72(1966), Black P. M., In Youmans J R (Ed.) *Neurological Surgery* 4th Ed. Philadelphia:W B Saunders, Vol 2, pp: 927–944(1996)). However, the coordinates defined relative to external landmarks can be subject to a great range of variation result of the unusual head size and shape or anatomical distortions. The ventricle size might be significantly small in some patients. Free hand technique also heavily depends on the surgeon's imagery, sense of spatial orientation and hand-eye coordination to find a correct trajectory toward ventricle. In addition, the head stays under surgical drapes during surgery which covers all external landmarks. Furthermore, the head may not be in a neutral position during surgery depends on surgical approach and this make spatial orientation more difficult. As a result, using external landmarks to find a proper entry point and trajectory is highly prone to error. Therefore, even optimum trajectory selection methods have serious limitations with free hand technique. As a result, the rate of success for a proper catheter placement depends on several factors such as surgeon's experience, size of the ventricles and surgical approach. Unsuccessful attempts, multiple passes of cerebral matter or suboptimal catheter placements with free hand technique are not very rare. This may cause increased morbidity and operation time.

Critical factors in proper placement of ventricular catheters are selection of proper burr hole site and determining the accurate trajectory from entry point to target point, accurate calculation of the length of the ventricular catheter and advancing the catheter precisely along the predetermined trajectory. The last factor emphasize the importance of supporting and holding of the catheter during the placement. Freehand technique relies on the inability of the surgeon to hold and advance the ventricular catheter or other neurosurgical instruments precisely along the predetermined position and trajectory. On the other hand it is obvious that manually supporting an instrument in a precise orientation does not guarantee that the trajectory will not be misrouted during advancement of the instrument. All stated information above for ventricular catheter placement technique is precisely relevant for any surgical intervention relates to unexposed intracranial target such as tumor biopsy, electrode placement, drainage of intracerebral collections.

These limitations of freehand technique caused development of a number of methods and devices. Several devices from very simple mechanical guides to very sophisticated frameless image guided neuronavigational systems are available to use during ventricular catheter placement or other surgical procedures which aim to reach an unexposed intracranial target (Garell P. C. et al, *J.Neurosurg.*89:157–160(1998), Howard M. A III et al.,*J. of Neurosurg.* 82:300–304(1995), Ghajar J. B. G. *J. Neurosurgery* 63:985–986(1985)). Readily available techniques and devices for guidance during similar surgical procedures are air ventriculogram, intraoperative fluoroscopy, simple right-angled ventricular guides, burr-hole localizers, stereotactic frames and image-guided neuronavigational devices.

Air ventriculogram has historical importance but not much place in modern neurosurgery. Intraoperative fluoroscopy is rarely used to localize and reach an unexposed intracerebral target, although it is useful to reach intracranial bony compartments such as sella.

A simple right angled frontal ventricular catheter guide has been developed by Ohajar J. B. G. *J. Neurosurg.* 63:985–986(1985). This device is constructed based on a simple anatomical fact that the lateral ventricles of the human brain form an arc parallel to the arc of the cranium. Thus, inventor assumed that a catheter guided perpendicularly to the cranium surface at the point of entry will enter the ventricular system. Specifically, any line penetrating a burr hole in the surface of the skull at a 90° angle also bisects the lateral ventricle. Howard et al. developed another device for parieto-occipital placement of ventricular catheter in a brain (Howard M. A. III et al., *J. of Neurosurg.* 82:300–304 (1995)). This rigid C-shaped device provides a linear trajectory between two surface landmarks, the burr hole and the frontal target site. They defined frontal target site as 1 cm superior to the supraorbital rim in the midline and parieto-occipital entry site as 3–4 cm above the inion and 2–3 cm lateral to midline. They claimed that a linear trajectory between these two points bisects the anterior horn of the ipsilateral lateral ventricle. Garell et al. later developed a posterior ventricular catheter burr hole localizer to prevent errors related to poor selection of posterior burr hole site (Garell P. C. et al., *J. of Neurosurg.* 89:157–160(1998)). It is obvious that these guides and similar methods rely on the correctness of some anatomical assumptions developed based on a perfect anatomy without any asymmetry or distortion. They also do not provide any objective data relates to distance between entry and target points. Finally, they were developed purely for placement of intraventricular catheters.

Stereotactic frames are the oldest and most widely used devices to localize and reach an unexposed intracranial target. Stereotaxis means a spatial arrangement which is fixing any point in space by application of mathematical principles (Bosch D. A., In Bosch D. A.(Ed.) *Stereotactic techniques,* Wien:Springer-Verlag, pp:9–41(1986)). Since Clark developed first stereotactic frame in 1906, numerous stereotactic frames were developed and used in humans (Bosch(1986)). Stereotactic localization methods also evolved during this period. In early years stereotactic maps of human brain were developed and used for stereotactic procedures. CT and MRI guided stereotaxy has been available for some years and replaced the old technique based on maps. This development allows us to reach any intracranial point with great accuracy.

The purpose of the stereotactic technique in human brain is localizing and reaching to a given intracranial target point precisely and without exposing the target. This includes a method which enables us to calculate the coordinates of an intracranial target point and the shortest and safest trajectory by selecting a proper entry point on cranium. This also includes a device which enables the neurosurgeon to orient, position and introduce the necessary instrument along the predetermined trajectory at a predetermined length placing the tip of the instrument into the target point. Modern stereotactic systems include a stereotactic reference frame, an aiming assembly and a method for calculating coordinates after CT/MRI image acquisition. Stereotactic reference frame provides rigid cranial fixation with pins and screws and establishes a sterotactic coordinate system in a physical space. Aiming assembly holds and directs the probe or other surgical instruments along the predetermined trajectory to a defined intracranial target point (Bosch(1986)).

Stereotactic techniques and devices have been used widely in neurosurgery for several purposes such as tumor biopsy, lesioning of deep targets, isotope implantation, drainage of intracranial collections, electrode and catheter placement.

Stereotactic frames have several drawbacks. It includes a rigid, bulky frame which might be severely restrictive and interfering the neurosurgeon's freedom of movement and range of motions during the procedure and uncomfortable for the patient. It is also relatively complicated and time consuming device to use. It is to be fixated with screws or pins to the patient's skull and CT/MRI image acquisition is needed with the frame just before surgery. This causes a significant time delay and an additional significant expense. Because of all these reasons, it is extremely cumbersome to use for short, simple procedures such as ventricular catheter placements.

More recently, physical space localization methods with sophisticated image-guided neuronavigational devices have been introduced. These are devices includes articulated mechanical arms, ultrasonic range finding systems, electro-magnetic systems, and active and passive optical techniques (Heilbrun M. P., In Youmans J R (Ed.) *Neurological Surgery* 4th Ed. Philadelphia:W B Saunders, Vol 1, pp:786–794 (1996)). All neuronavigational systems use extrinsic skin-affixed or bone-implanted markers or anatomical structures to determine rigid body registration transformation. Neuronavigational devices provide a precise virtual surgical guidance based on preoperative image data. This application has some disadvantages such as movement of the head and brain during surgery, positional shift and inaccuracies related to intraoperative displacement and deformation of the brain during surgical procedures. In addition, these devices are rather complicated to use, extremely expensive and unnecessarily time consuming for some short procedures. Not having an instrument holder and guide to provide a precise guidance to an intracranial target after localizing it with a probe is a significant disadvantage of some of these frameless neuronavigational devices.

Although recently some neuronavigational devices started to include an instrument guide or attachments to the surgical instruments to continue providing guidance, previous models and most of the current models still do not provide any instrument guidance. The neurosurgeon can see virtual trajectory to any intracranial target point on screen, whenever he/she removes the probe and try the follow same trajectory, he/she actually has to use his imagery spatial orientation. Therefore, neurosurgeons still has to face limitations of freehand technique to advance the instrument after seeing the trajectory on the screen of the neuronavigational devices.

Thus all the methods and devices described above here-tofore known suffer from a number of disadvantages. These are either highly prone to error such as in the freehand technique, invasive and uncomfortable for the patient or restrictive for surgeon such as in classical stereotactic frames or very expensive, complicated and time consuming for simple procedures such as in neuronavigational devices. Therefore, there is a need for a device which is easy to learn, simple to use, rapid, inexpensive, versatile and accurate, comfortable for the patient and non-obstructive for the surgeon. There is also a need for an associated method which can provide target coordinates for each patient based on CT/MRI images and will not require a separate image acquisition with frame.

OBJECTS AND ADVANTAGES

We developed a method and device for some neurosurgical interventions related to unexposed intracranial targets, more specifically for (i) guidance and placement of ventricular catheters and intracranial pressure (ICP) monitoring electrodes, (ii) guidance and placement of surgical instruments to have biopsy specimen from unexposed intracranial lesions, (iii) guidance and placement of surgical instruments to drain unexposed intracranial collections, (iv) holding a surgical instrument exactly in a same precise trajectory determined by an image guided neuronavigational device, (v) marking the scalp and craniotomy flaps on the patients head based on the coordinates of an unexposed intracranial lesion.

The objects and advantages of the present invention are: (a) to provide a device which is easy to learn, simple to use, inexpensive, non-invasive, comfortable for patient, non-obstructive for surgeon, versatile, accurate and does not cause intraoperative time delay, (b) to provide a method for localizing the coordinates of a defined intracranial target point and an entry point relative to external anatomical landmarks or fiducial markers on the patients CT/MRI images, (c) to provide a method and device to use both external anatomical cranial reference points and fiducial markers on CT/MRI, (d) to provide a method and device which enable the surgeon to transfer the calculated coordinates of entry and target points to the stereotactic frame and check the accuracy of the set up before transferring the coordinates to the patient's head, (e) to provide an intermediary device to transfer the coordinates of the predetermined trajectory from stereotactic frame by enabling the surgeon having reproducible trajectory from the same entry point without having restrictions and obstructions of stereotactic frame, (f) to provide a device for holding and guiding surgical instruments along the predetermined trajectory toward the intracranial target point.

Further objects and advantages are to provide guidance to direct placement of scalp and craniotomy flaps properly by providing a method and device which will allow selection of multiple entry points and targets, and to provide a device for holding and guiding surgical instruments along the trajectory determined by the probes of neuronavigational devices, endoscopes and similar instruments. Still further objects and advantages will become apparent from a consideration of the ensuing description and drawings.

LIST OF REFERENCE NUMERALS

Figure 1:
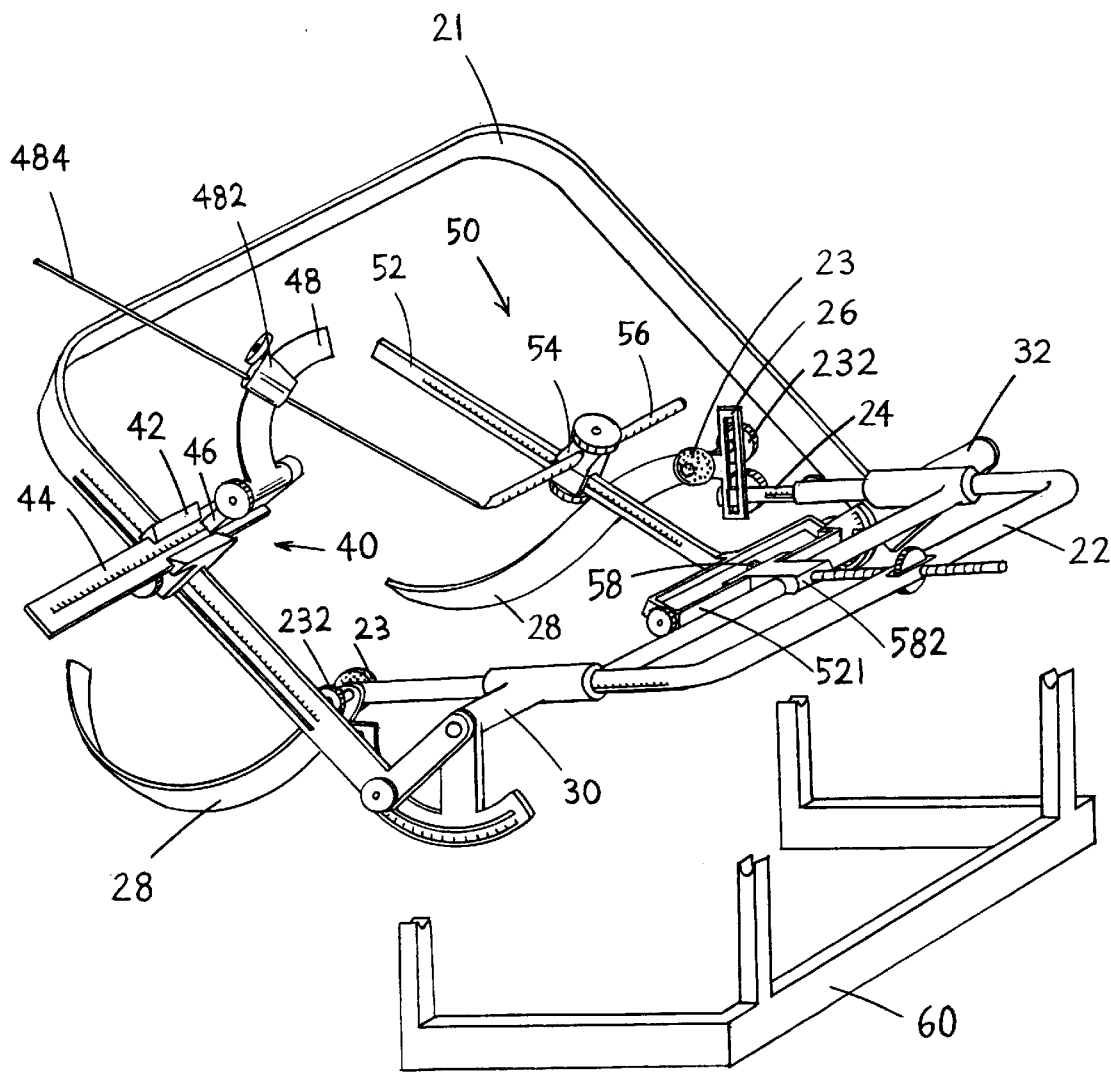
FIG. 1 shows the adjustment apparatus directly above its stand.

20 Patient's head
21 Main Rail Frame
22 Secondary Frame
23 Lateral fiducial Pieces
232 Lateral fiducial Screws
234 Lateral fiducial Screws for Infant
24 Extension Piston
26 Height Adjuster Rack
28 Support Bands
30 Target Assembly Holder Right
32 Target Assembly Holder Left
40 Guidance Assembly
42 Main Guide Holder
44 Sliding Guide Support
46 Upright Support
48 Pointer Support Arch
482 Pointer Guide
484 Pointer
486 Axis of rotation of the Pointer Support Arch
488 Center of the arch represented by the Pointer Support Arch
50 Target Assembly
52 Target Arm
521 Target Arm Base
522 Frontal Axis
524 Rear Axis
54 Target Localizer Support
544 Rear Axis
56 Target Localizer
58 Nose-Bridge Piece
582 Central Target Arm Holder
60 Stand
70 Portable guider
72 Portable guider Barrel
728 Portable guider Barrel with Narrow Shaft
729 Portable guider Barrel with Wide Shaft
74 Portable guider Sphere
741 Portable guider Sphere Center
75 Portable guider Ring
76 Portable guider Leg
78 Portable guider Foot
781 Portable guider Toe
782 Portable guider Tack
80 CT/MRI Output
82 Slice
824 Slice Centerline 825 Point "a": Nasion
826 Point "b": External auditory meatus
827 Point "e": Entry Point
828 Point "t": Target Point
829 Distance "at": Length of the line connecting the Nasion and Target Point on the plane of the patient's profile.
830 Distance "ae": Lenght of the line connecting the Nasion and Entry Point on the plane of the patient's profile.
831 Distance "ab": Length of the line connecting the Nasion and the External auditory meatus on the plane of the patient's profile.
832 Angle "bat": Target Angle
833 Angle "bae": Entry Angle
834 Distance "me": Shortest distance from Entry Point to Slice Centerline on the plane on the Slice.
835 Distance "mt": Shortest distance from Target Point to Slice Centerline on the plane on the Slice.
836 Point "x": Location of Anterior fiducial
837 Point "y": Location of Lateral fiducial
838 Offset Centerline of Slice
839 Distance "mx": Shortest distance from Point "x" to Slice Centerline.
840 Point "c": External auditory meatus on the opposite side of patient's head.
841 Curve "v": Curve passing through the endpoints of the Centerlines of all Slices. This curve vertically divides the upper part of the head approximately into two halves.
842 Distance "xt": Length of the line connecting the Anterior fiducial and Target Point on the of the patient's profile.
843 Distance "xe": Lenght of the line connecting the Anterior fiducial and Entry Point on the of the patient's profile.
844 Distance "xy": Length of the line connecting the Anterior fiducial and the Lateral fiducial on the plane of the patient's profile.
845 Angle "yxt": Target Angle used in the operation with markers
846 Angle "yxe": Entry Angle used in the operation with markers
850 Distance "ef": Length of line from the projection of Point "e" on the slice centerline to the front of slice.
852 Distance "tf": Length of line from the projection of Point "t" on the slice centerline to the front of slice.
854 Point "u": The point where the shortest line from opposite, external auditory meatus 840 to the line passing through the external auditory meatus and nasion intersects that line.
860 Distance "H": Distance between the top of the pointer guide 482 and the tip of the pointer 484 when it coincides with the target point.
862 Distance "K": Distance between the top of the pointer guide 482 and the top of portable guider barrel 72 when portable guider is placed on the patients's head.
836 Straight line passing through Points "a" and "b" 825,826
664 Distance "L": Distance between the top of the portable guider barrel 72 and the tip of the pointer 484 when it coincides with the target point when portable guider is placed on the patients's head.
902–918 Scales permanently fixed on the apparatus in order to adjust the movable part to desired
distances and angles.
94 Catheter
98 Biopsy forceps
1002 Ventricle Boundary
1004 Lesion Boundary
1006 Mark made on Skin
1007 Marker

SUMMARY

The invention provides a method of (i) rapidly and accurately localizing an entry and an unexposed intracranial target point and (ii) reliably, easily and accurately guiding surgical devices from the entry point to the target point with minimal intrusion in surgery. As a natural extension of (i) the invention also provides a method of marking the boundaries of specific regions on the surface of the patient's head. The present method and instrument use the natural reference points or images of fiducial markers found in outputs from CT or MRI of the patient's head. Briefly put, the invention works by gathering data from neuroimaging studies, such as CT/MRI, mechanically adjusting an apparatus based on the data, and transferring all this information to the settings of an adjustable portable guider. The portable guider is the only part of the invention that is employed during the surgery.

DETAILED DESCRIPTION OF THE PHYSICAL EMBODIMENTS

Figure 6A:
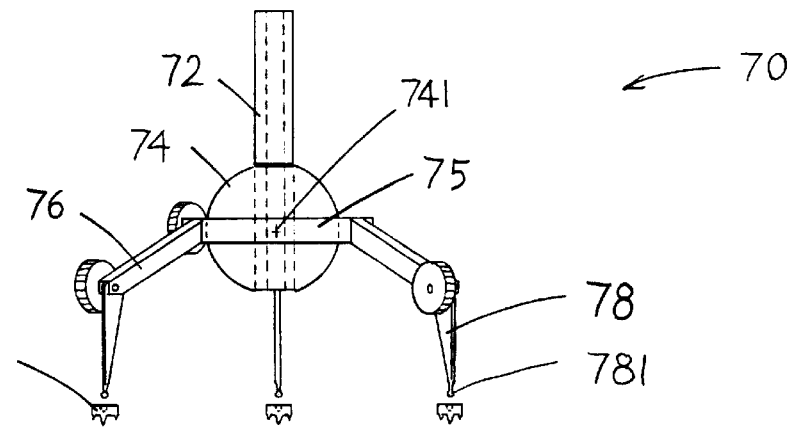
FIGS. 6A–C show the portable guider 70.
Figure 6B:
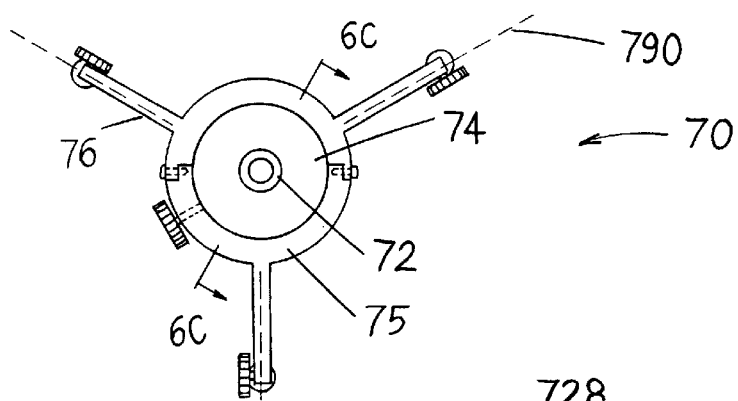
Figure 15:
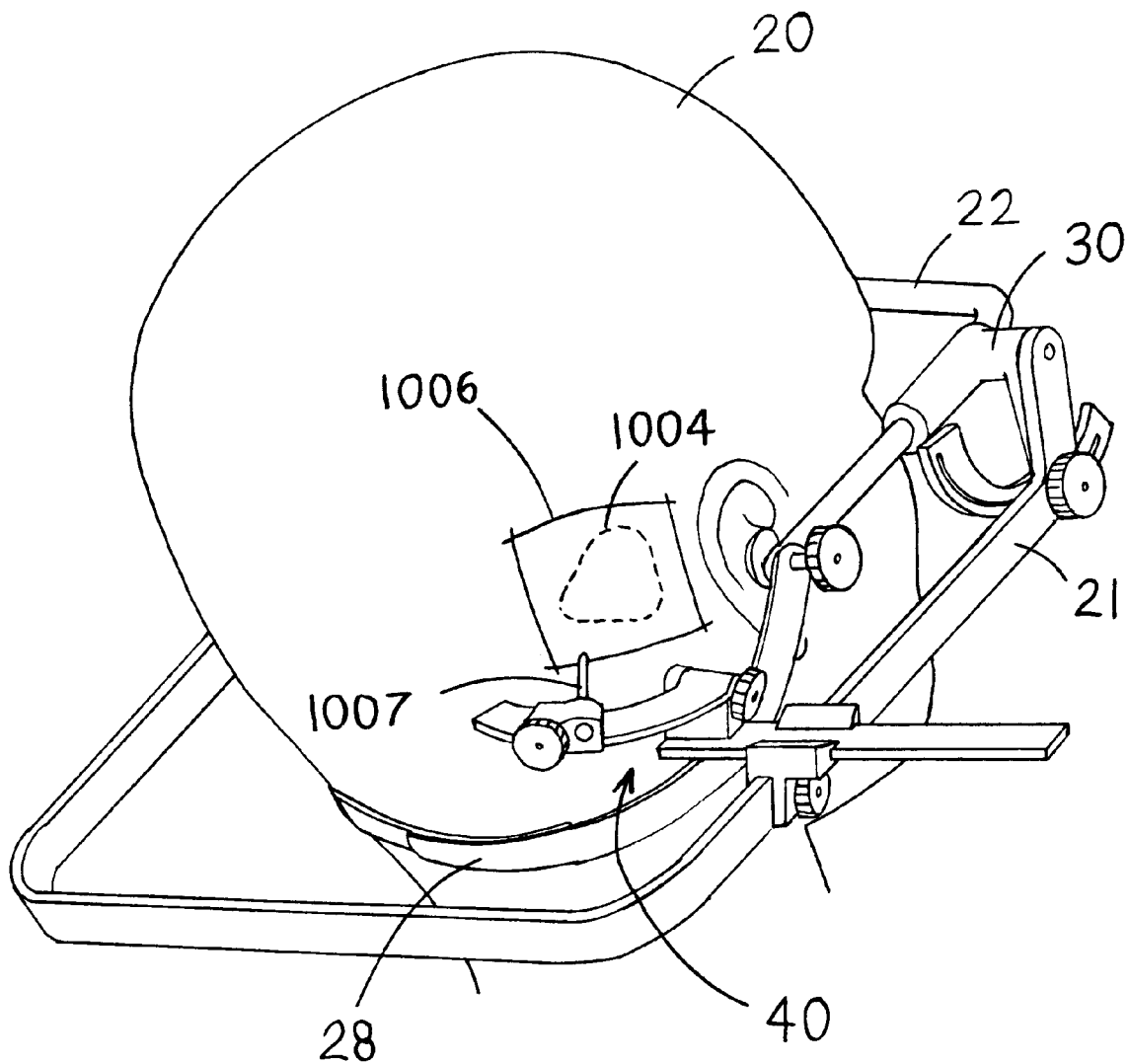
FIG. 15 shows the adjustment apparatus installed on patient's head for marking the boundaries of a deep-seated lesion on the surface of the head.

The physical realization of the invention consists of two main components: The adjustment apparatus and the portable guider. All parts of the the adjustment apparatus referred to as "apparatus" appear in FIG. 1. The portable guider 70 is shown in FIG. 6A and FIG. 6B. Together they are referred to as the guidance system referred to as "system". In this section, the two parts of the system will first be described in detail In the descriptions below, what is called the front, the back, the left, and the right sides of the apparatus are determined with respect to a the patient's head shown in FIG. 13A, FIG. 13B, and FIG. 15.

Adjustment Apparatus

The apparatus consists of two main sections. The first has to do with the localization of the entry point. The second has to do with the localization of the target point. The entry point is localized by means of the main rail frame 21 and the guidance assembly 40. Referring to FIG. 1, the main rail frame 21 is an approximately U-shaped frame with short upturned extensions at both open ends. The arms of the U-shape generally point toward the front and are attached with pin connections to the target assembly holders 30,32. The right target assembly holder 30 has an extension for measuring the orientation of the main rail frame 21 and fixing it at a desired angle.

Figure 5:
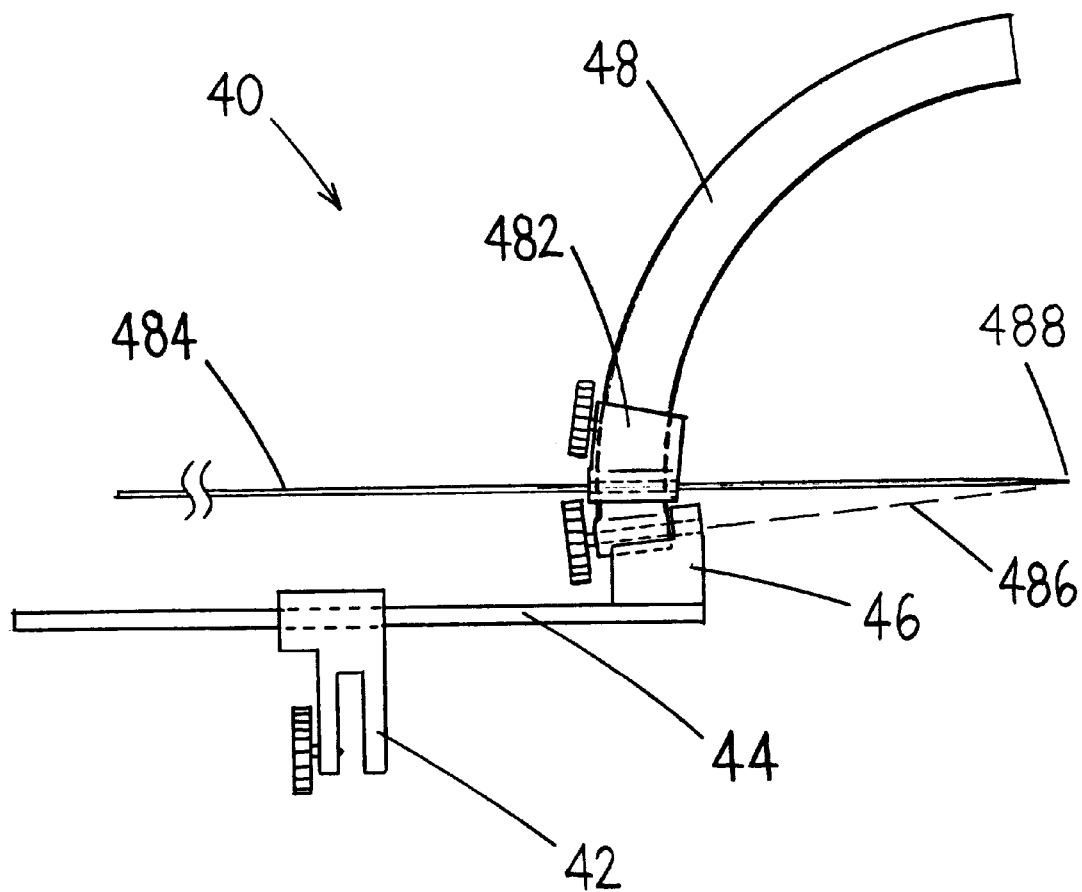
FIG. 5 is the side view of the guidance assembly.

When the main rail frame is fixed at the desired angle it establishes a plane on which the guidance assembly 40 is able to slide over a wide range of positions. The guidance assembly 40 shown in FIG. 1 also appears in top view in FIG. 2 and in detailed side view in FIG. 5. The main guide holder 42 engages and is able to slide on the main rail frame 21. It can be removed and installed on either side of main rail frame in order to function on either side of the patient's head. On the main rail frame the guidance assembly can be fixed at a desired position. The sliding guide support 44 is shaped in the form of an elongated and flat rectangular prism and fits into the slot in the main guide holder 42. The rest of the guidance assembly 40 is mounted on the sliding guide support. Therefore the guidance assembly, except for the holder 42, can be displaced as much as necessary along a direction perpendicular to the arm of the main rail frame.

The upright support 46 is welded or otherwise permanently fastened to the sliding guide support 44. The pointer support arch 48 is attached to the upright support by a screw that can be tightened manually. The screw lies on the axis of rotation 486 of the pointer support arch indicated in FIG. 5. In the side view in FIG. 5 the axis of rotation 486 of the pointer support arch is oriented at an angle relative to the sliding guide support 44. This is needed so that a pointer 484 is able to have a wider range of positions on the sliding guide support 44.

The pointer support arch 48 is able to rotate, within a range of approximately 270 degrees, about its axis of rotation 486. To visualize this rotation, note that the top of the pointer support arch 48 would move into and out of the page in FIG. 5 as it rotates about its axis 486. After being rotated to a desired angle about its axis, the pointer support arch can be fixed at the desired angle. The pointer guide 482 is able to slide on the pointer support arch 48. The pointer guide contains a cylindrical hole through which the pointer 484 can be inserted. The pointer is a thin cylindrical metal rod confined to remain in the orientation determined by the pointer guide. By elementary geometry, regardless of the angle of the support arch and of the position of the pointer guide on the pointer support arch, the pointer guide 484 always passes through the arch center 488. In a properly adjusted system, the arch center 488 will coincide with a previously determined entry point 827 shown in FIGS. 7–10.

Figure 3:
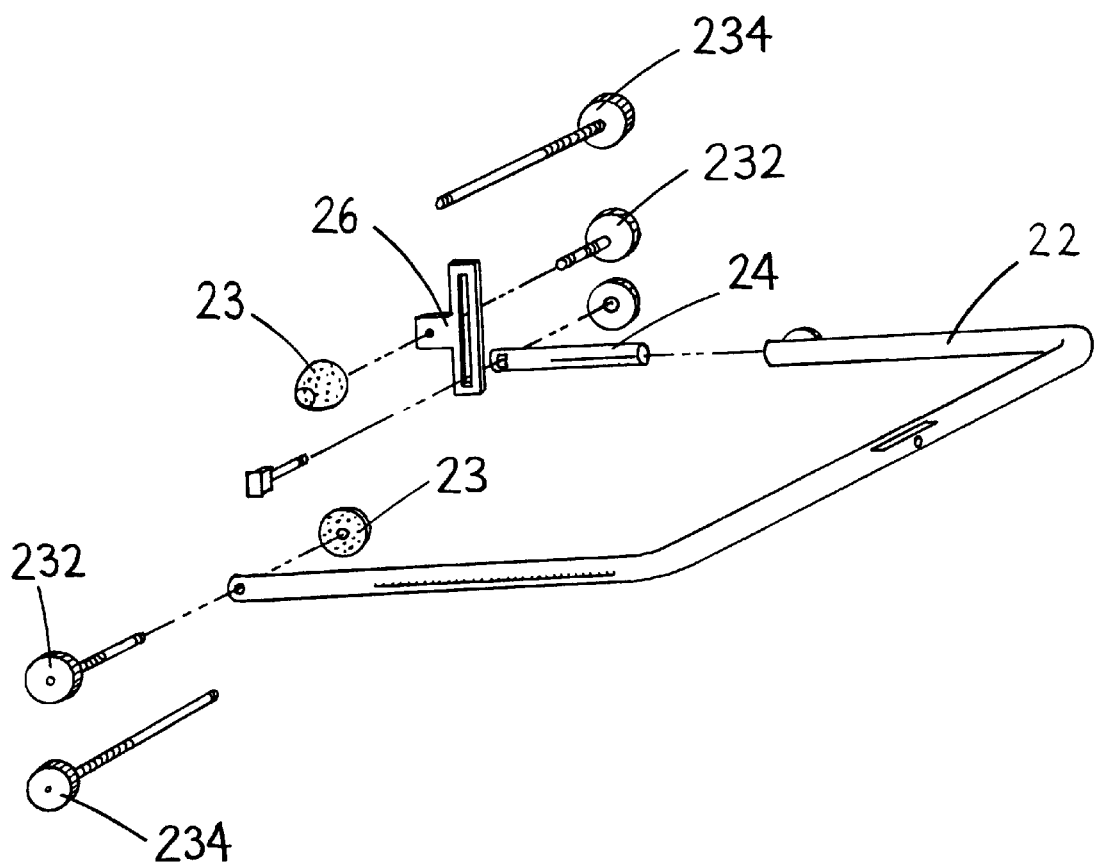
FIG. 3 represents an exploded view of the components of the secondary frame 22

The target assembly holders 30, 32 are able to slide together on the secondary frame 22. FIG. 3 indicates the basic shape and components of the secondary frame. It is approximately U-shaped with a slot and cylindrical hole at the bottom segment of the U-shape. The bottom segment of the approximate U-shape is at the front. The right lateral fiducial piece 23 is attached to the right end of the secondary frame. The lateral fiducial pieces 23 can be adjusted to fit snugly and tightly to the external auditory meatus or to the lateral fiducials on both sides of the patient's head. The left end of the secondary frame 22 contains a cylindrical opening slot where an extension piston 24 is inserted as shown in FIG. 3. A groove on the extension piston 24 which slides into a slot in the secondary frame insures that the cylindrical extension piston does not rotate about its longitudinal axis. The extension piston moves inside the left arm of the secondary frame in telescope fashion without rotating and it can be fixed at any desired position relative to the secondary frame.

Figure 2:
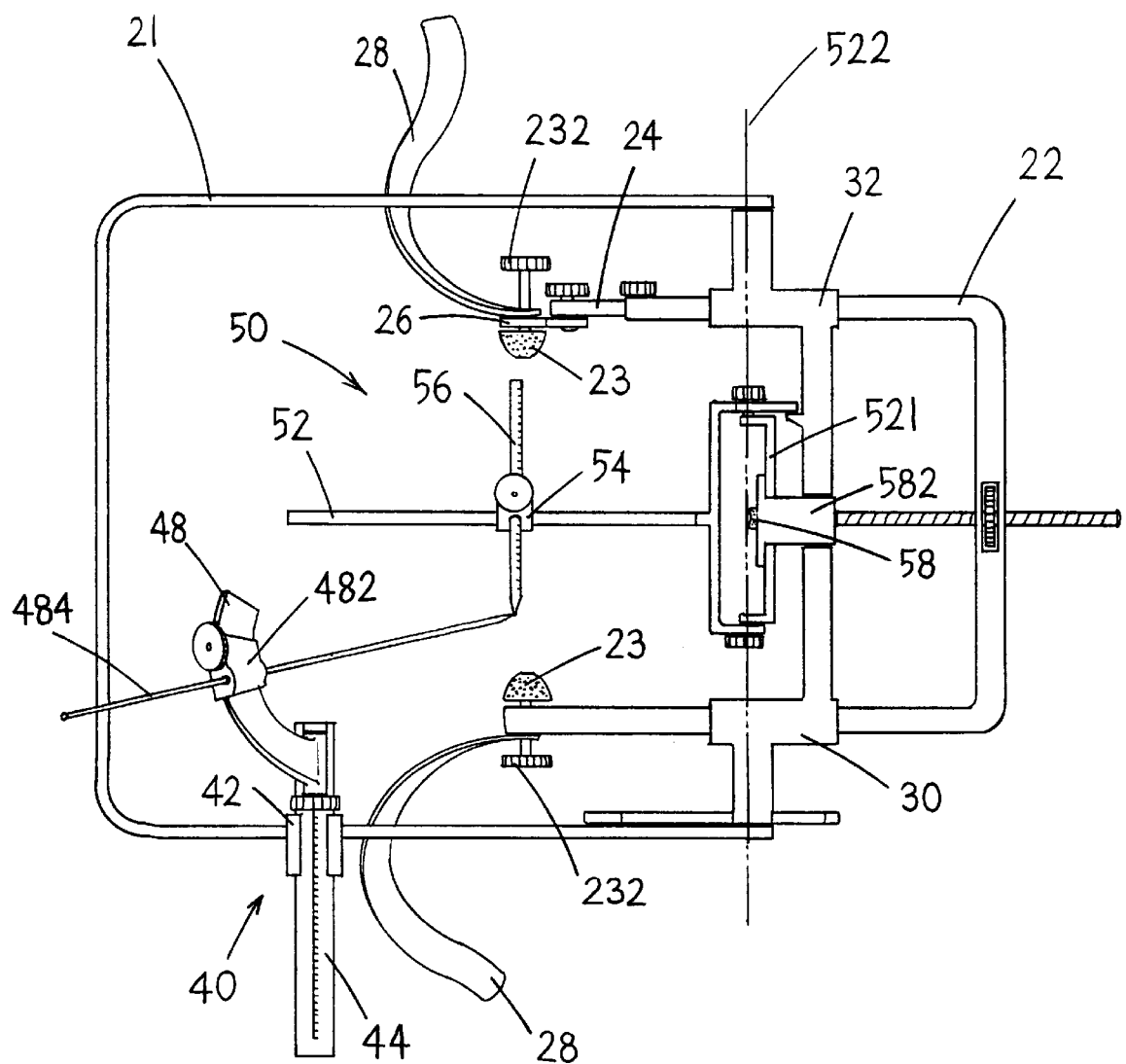
FIG. 2 is the top view of the adjustment apparatus with the main rail frame and target arm in the horizontal position.

A height adjuster rack 26 is attached to the extension piston as seen in FIGS. 1–3. The height adjuster rack is able to move in a direction which is vertical to the plane determined by the U-shape of the secondary frame 22. It can be fixed at a desired height relative to this plane. The left lateral fiducial 23 is fixed on the height adjuster rack.

Figure 4:
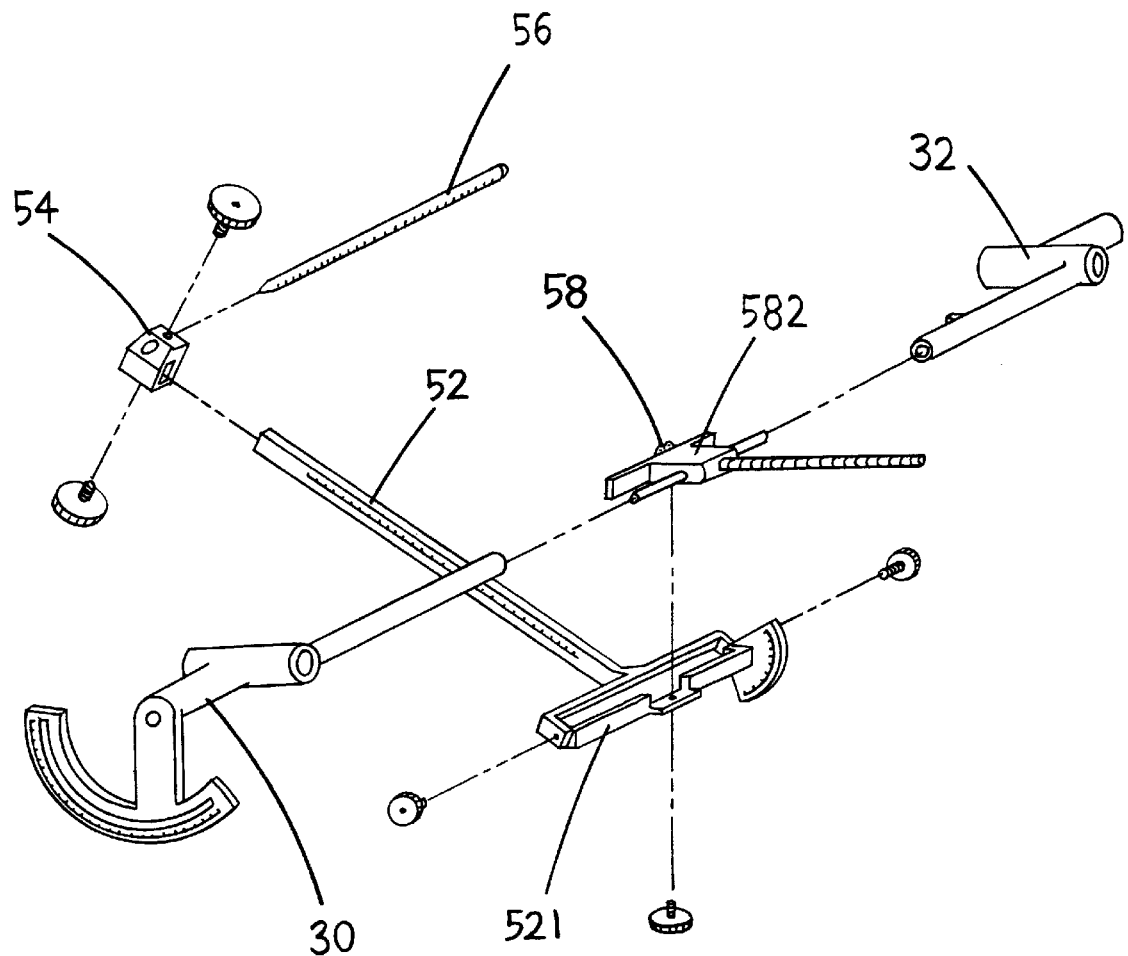
FIG. 4 shows an exploded view of the target assembly holders 30, 32 and the target assembly 50.

The target point is localized by means of a target assembly 50 shown in exploded view in FIG. 4. The target assembly contains a target arm base 521 which is fixed on to a central target arm holder 582. The main body of the central target arm holder is shaped approximately as a rectangular prism. It has two thin cylindrical extensions at the sides which are inserted into the target assembly holders 30, 32. The central target arm holder has an adjustment screw at the front which fits into the slot in the front section of the secondary frame 22 as seen in FIGS. 1–2. The target assembly holders 30,32 are able to move back and forth in the plane of the secondary frame 22. Therefore the position of the target assembly relative to the secondary frame can be adjusted and fixed by means of the adjustment screw on the target arm holder. A nose piece 58 is attached to the central target arm holder 582. The nose piece can be displaced and fixed on a desired horizontal position on the central target arm holder. FIGS. 1,2, and 4 show the nose piece 58 positioned at the middle of the target assembly.

The target arm base 521 is secured by means of a metal bolt to the bottom of the central target arm holder 582. During a part of the operation of the system this bolt is removed and the target assembly 50 is separated from the apparatus.

The target arm 52 is connected to the target arm base by two pins which lie on the frontal axis 522 indicated in FIG. 2. The frontal axis is also the common axis of the pins that connect the main rail frame 21 to the target assembly holders 30,32. Looking somewhat ahead to the explanation of the basic invention, the frontal axis 522 appears as the point "a" in FIG. 7 and point "x" in FIG. 8. Returning to the physical description of the apparatus, the target arm freely rotates about the frontal axis and can be fixed at a desired angle. The value of this angle is shown on the piece shaped as a section of a circle fixed on the target arm 52 by an indicator protruding from the left target assembly holder 32.

A target localizer support 54 fits and is able to slide on the target arm 52 as seen in FIGS. 1,2, and 4. A target localizer 56 in the from of an elongated cylindrical rod slides into the target localizer support. The position of the target localizer support 54 on the target arm 52 and the position of the target localizer 56 on the target localizer support 54 can both be independently adjusted and fixed. At one stage of the operation of the system, the pointed tip of the target localizer 56 will coincide with the target point 828 which appears in FIGS. 7 and 8. The target localizer is shown pointing toward the right in FIGS. 1, 2, and 4. However, the target arm 52 and the slot in the target localizer support 54 are left-right symmetric. Therefore the target localizer support can be inserted on the target arm 52 to point either toward the right or toward the left.

The tips of the lateral fiducial pieces 23 and the nose piece 58 are made of a firm elastic material which produces non-injurious and tight contact with the natural cavities on the head. They also have small circular cavities at their tips in order to fit tightly to small markers fixed on the skin. The support bands 28, shown in FIGS. 1 and 2, are made of cloth or of vinyl with velcro adhesion surfaces at the free ends. The lateral fiducial and nose pieces and the support bands 23,28,58 are the only components of the apparatus that contain any non-rigid materials. The rest of the system is preferably made of very hard and resistant metals commonly used in surgical instruments.

Portable Guider

Figure 6C:
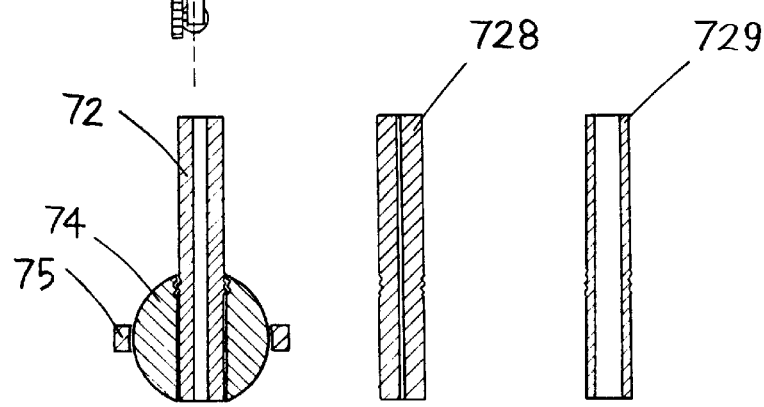

The portable guider shown in FIG. 6 contains a portable guider sphere 74 which fits into the portable guider ring 75. The portable guider ring allows the portable guider sphere to rotate about its center 741 but allows no other displacements. A portable guider barrel 72 can be manually screwed into a cylindrical hole inside the portable guider sphere. The portable guider barrel contains a cylindrical hole along its longitudinal axis. A number of portable guider barrels containing holes with different diameters are needed in the operation of the system in order to accomodate various medical instruments.

The vertical thickness of the portable guider ring 75 is very small relative to the diameter of the portable guider sphere. This allows the sphere to rotate freely within a wide range of solid angles while the portable guider barrel 72 is attached to the portable guider sphere 74. Therefore the portable guider barrel can be oriented within a wide range of solid angles. The orientation of the portable guider barrel can be fixed by means of an adjustment screw in the portable guider ring 75 as seen in FIG. 6.

The portable guider ring 75 has three portable guider legs 76 welded or otherwise fastened permanently to it. As shown in FIG. 6A the portable guider legs are separated equally by 120 degrees around the portable guider ring. Each portable guider leg has a portable guider foot 78 attached to it by a pin. Each portable guider foot can be independently rotated about the axis of the pin and fixed at a particular orientation by means of an adjustment screw. In the fully vertical position each portable guider foot 78 points directly downward perpendicular to the plane defined by the portable guider ring 75.

Each portable guider foot has at its end a small spherical portable guider toe 781. By manually applying pressure to the portable guider, the portable guider toes can be fixed in and removed from the corresponding small circular cavities in the portable guider tacks 782. Since each portable guider foot can be independently adjusted for orientation, the position of each portable guider tack can be chosen freely and independently on the line segment defined by the portable guider tack locus 790. The portable guider tack loci 790 are the set of points where the portable guider tacks 782 may be placed while all of them remains accessible to the portable guider feet 781. In general the portable guider will rest on a surface that is irregularly shaped. Viewed from the top the portable guider tack loci appear on any surface as straight line segments emanating from a common center and whose orientations differ by 120 degrees as seen in FIG. 6B.

The spherical portable guider toe 781 is connected to the portable guider foot 78 by the small cylindrical tip of the portable guider foot whose diameter is much smaller than the diameter of the portable guider toe. This ensures that the portable guider toe 781 can snap into and out of the portable guider tack 782 even when the portable guider foot is in a highly slanted position. The top of the portable guider tacks are preferably made of a hard plastic to allow firm placement and removal of the portable guider toes 781 only by applying pressure to the portable guider. With this exception the portable guider is preferably made of very hard and resistant metals commonly used in surgical instruments.

Operation of the Invention

The surgeon applies the following step-by-step procedure in using the present invention. The first 4 steps are performed before the surgery:

Step 1. Measure the values of various distances and angles on the standard CT/MRI images of the patient.

Step 2. Using these values adjust the apparatus while it sits on its stand.

Step 3. Remove the target assembly 50 and the pointer 484 from the apparatus and install the apparatus on the patient's head.

Step 4. Place the portable guider between the guidance assembly 40 and the patient's head; adjust and fix the portable guider and place the portable guider tacks 782 on the anesthesized patient's head; then remove the system from the patient's head.

Step 5. In surgery, place the portable guider in its predetermined location and use it to guide a surgical device through the entry point to the target The functioning of the invention based on the above list of steps is now described in detail Step 1

Figure 7:
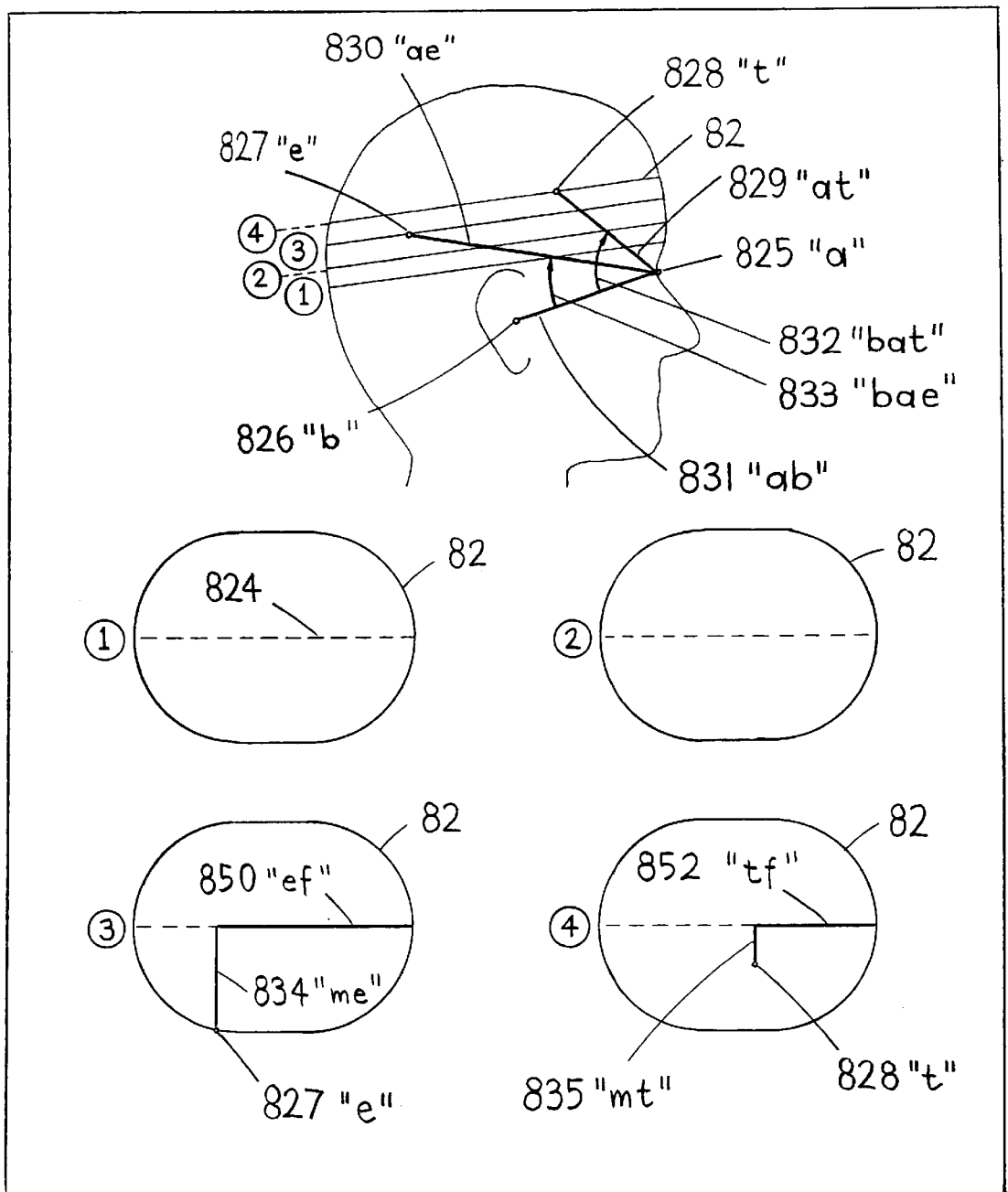
FIG. 7 represents the standard output obtained from CT/MRI along with the distances and angles measured by the surgeon prior to employing the guidance system—nasion and external auditory meatus are used as reference location indicators.

FIG. 7 shows a standard CT/MRI output. The profile image at the top contains lines which represent the side views of a set of slices 82. Slices are images of cross-sections of the patient's head which are all parallel and nearly horizontal Each slice is numbered and appears below the profile as one of the nearly elliptic images. The anatomical details which normally appear in these images have been omitted from FIG. 7 for purposes of clarity. There is generally a large number of slices which are spaced more closely about every 5 mm than what is shown in FIG. 7. The slice centerlines 824 are determined with great accuracy based on the anatomical details that appear in the images. The dark solid lines on the image represent the measurements that will be made by the surgeon.

Based on his/her judgement of the surgical needs of the patient, the surgeon first choose an entry point 827 and a target point 828 on the CT/MRI output. By using the slices where thee points are found slice 3 and 4 in FIG. 7 the distances "me" 834 , "mt" 835, "ef" 850 , and "tf" 852 are measured. Using the values of "ef" and "tf" the entry point 827 and the target point 828 are located and marked on the profile image. This is done, for the entry point, by starting at the front end of the line representing the slice 3 on the profile and going back by the amount "ef". Similarly for the target point. On the profile image in FIG. 7, the external auditory meatus 826 and the nasion 825 are also located. Then the distances "ab" 831 , "ae" 827 , and "at" 829 and the angles "bae" 833 and "bat" 832 are measured.

Figure 9:
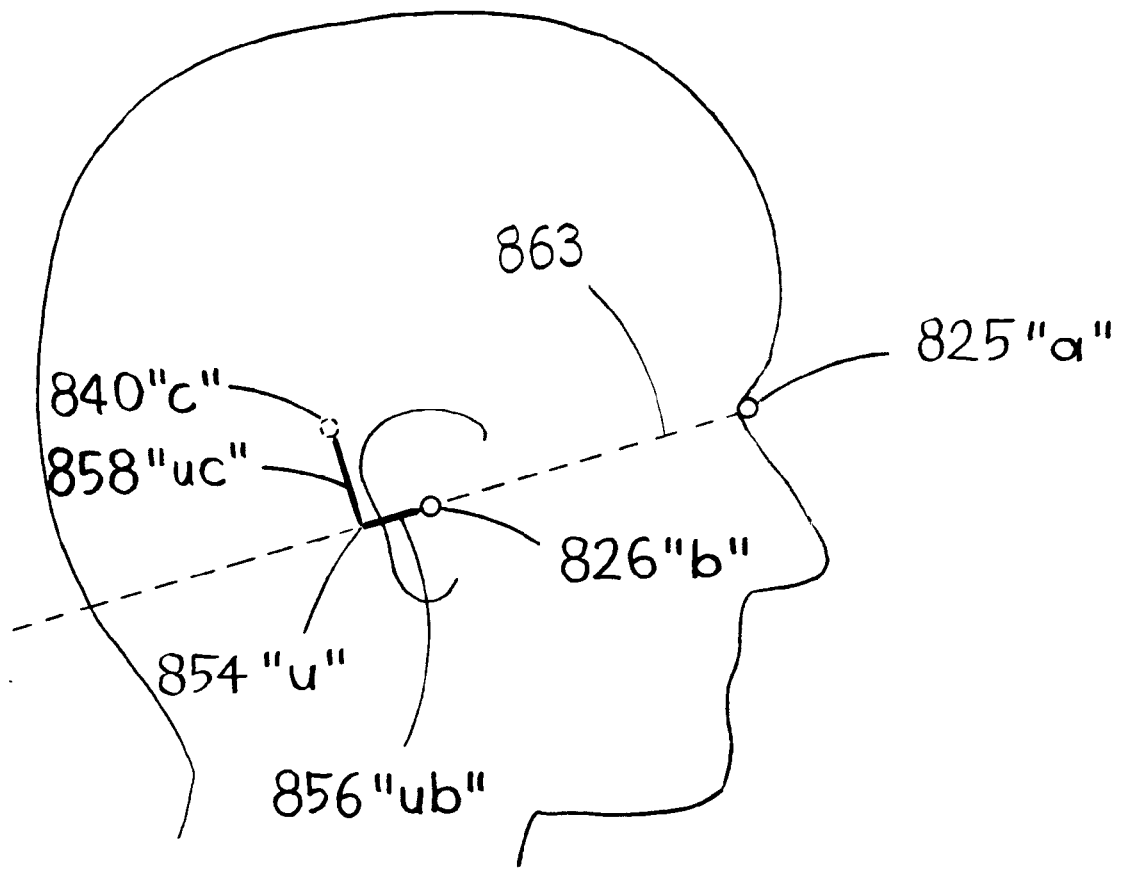
FIG. 9 shows the portion containing the image of the patient's profile in the standard output from CT/MRI with the offset distances between the external auditory meatus.
Figure 10:
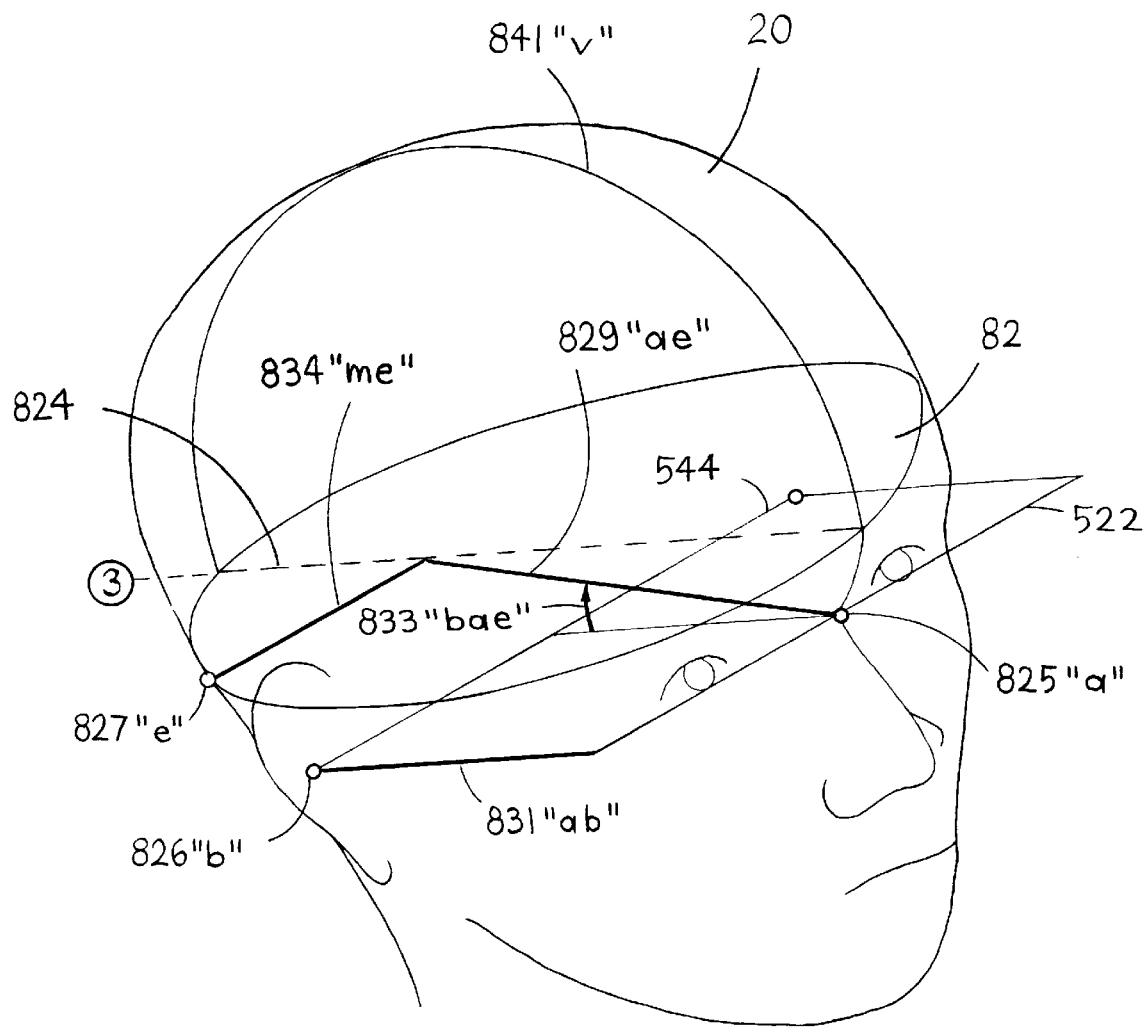
FIG. 10 illustrates the three dimensional geometric relationships among the distances and angles measured on CT/MRI output including the slice which contains the entry point 827.
Figure 11:
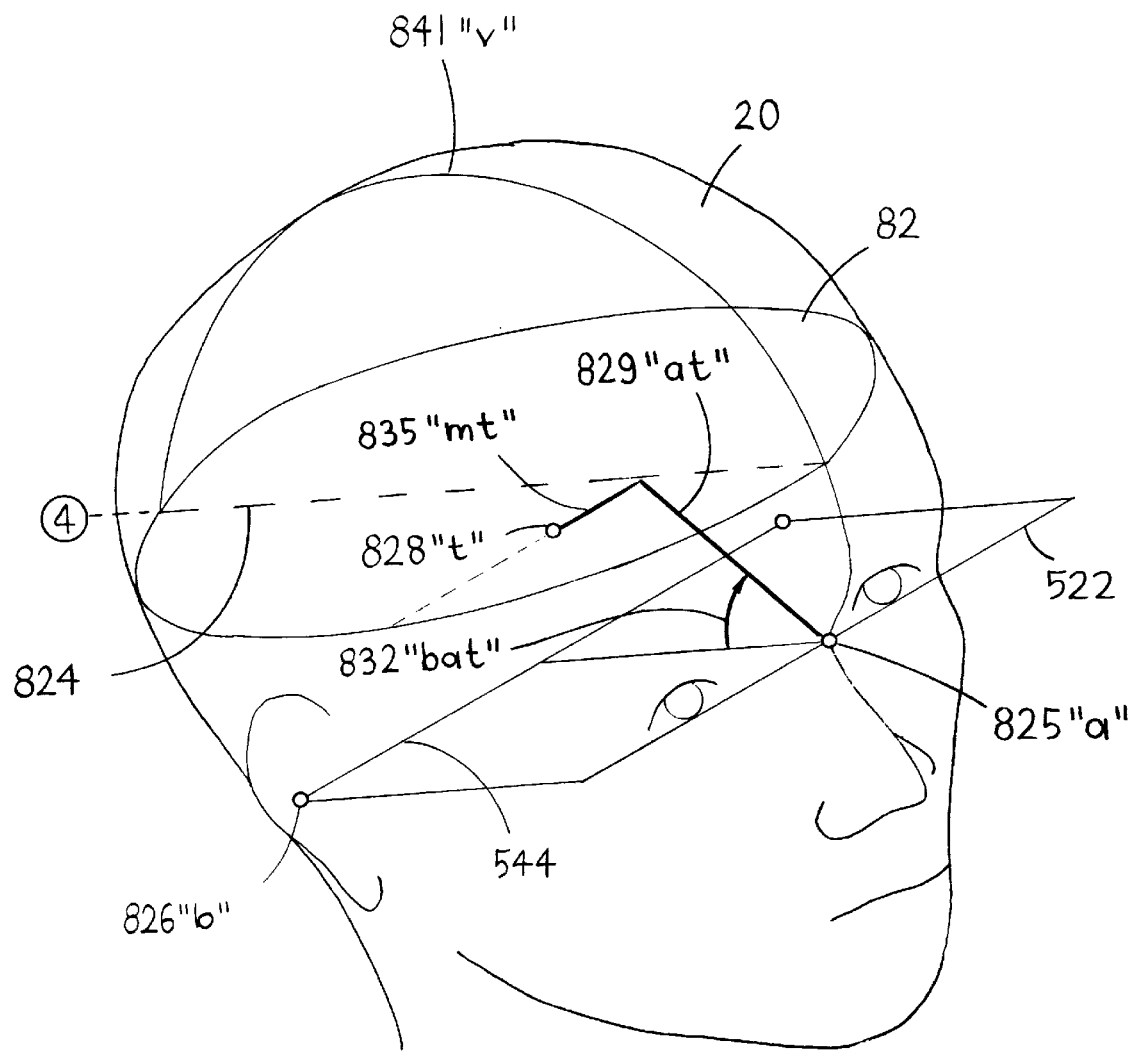
FIG. 11 illustrates the three dimensional geometric relationships among the distances and angles measured on CT/MRI output including the slice which contains the target point 828.

In general the external auditory meatus on the opposite side of the head will not coincide on the profile image with the external auditory meatus on the viewer's side 826. This situation is depicted in FIG. 9 where the opposite external auditory meatus 840 is shown by a dashed curve. When this nonalignment occurs the surgeon will measure the distances "ub" and "uc" 856,858 on the profile image.

Step 2

Figure 12:
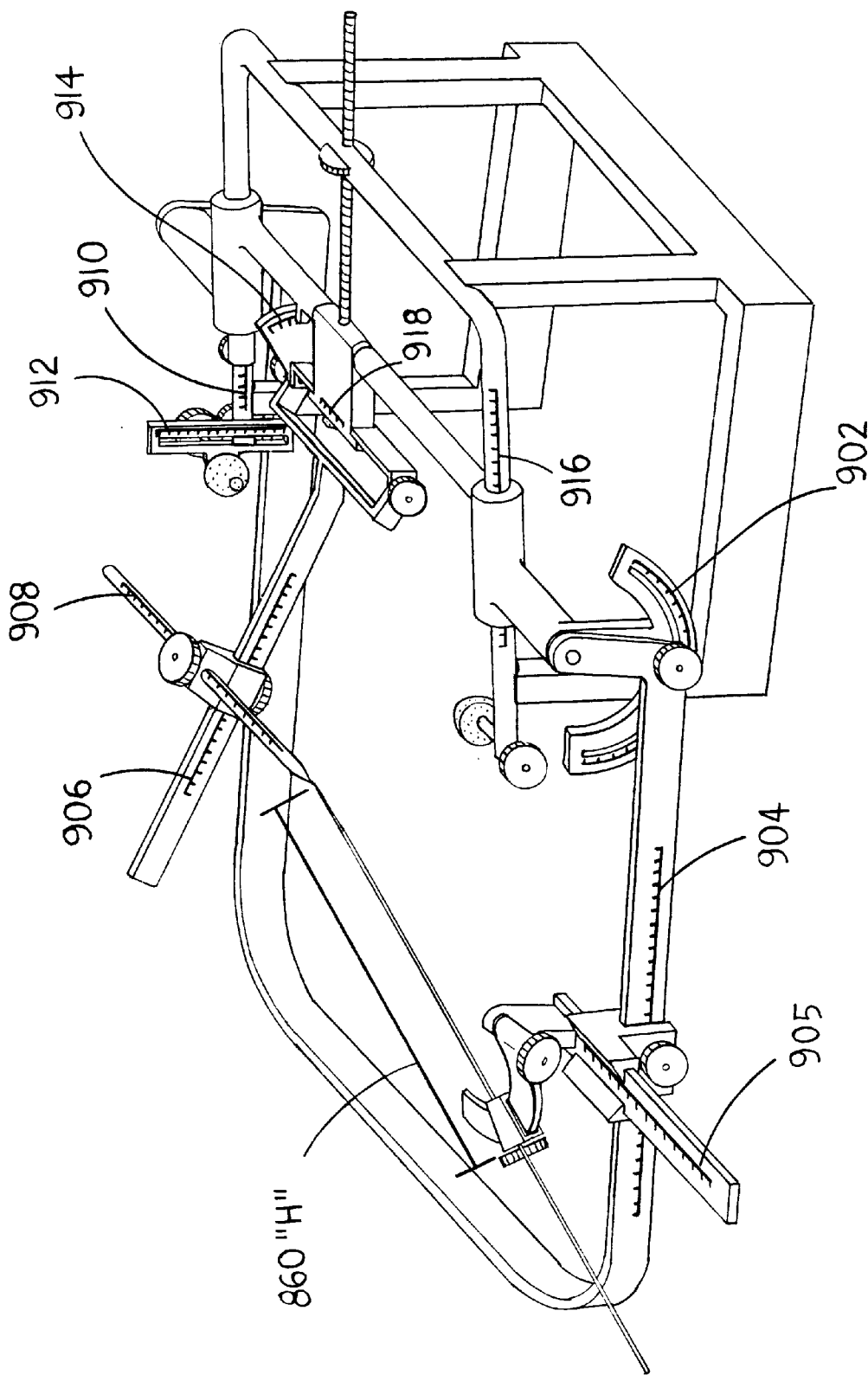
FIG. 12 shows the adjustment apparatus on its stand and the locations on the apparatus where adjustments are made based on measurements on the patient's CT/MRI output.

FIG. 12 shows the various scales that are marked on the apparatus. These markings on the scales are such that the values of variables measured by the surgeon on the CT/MRI output can immediately be adjusted as the position or the angle of some part of the apparatus. For example consider the scale 906 on the target arm 52. Suppose that the target arm 52 has been fixed at the angle "bat" 832 with respect to the plane of the secondary frame 22. Then as the target localizer support 54 slides on the target arm there will be a specific position where the centerline of the target localizer 56 will pass through the target point 828. The origin of the scale 906 is permanently placed in such a way that when this happens the reading at the edge of the target localizer support on scale 906 always indicates the value measured for the distance "at" 829 FIG. 7. The scales 902–918 shown in FIG. 12 all have their origins constructed in this fashion.

For brevity, "adjusting" a scale refers to bringing the part that slides on the scale to the desired position or angle and fixing it by an adjustment screw. While the apparatus sits on its stand 60 the following adjustments are made.

The scales 910 and 912 are adjusted using the values of "uc" and "ub", respectively. This insures that if the ear-sidemarker pieces were placed in the patient's external auditory meatuss the plane of the main rail frame 21 would be perpendicular to the plane of the profile in FIG. 7. Then the rear axis 544 in FIG. 10 would coincide with the external auditory meatus or the point "b" in FIG. 7. The frontal axis 542 in FIG. 10 would coincide with the nasion or the point "a" in FIG. 7.

Next the angle "bae" 833 is adjusted on scale 902, distance "ae" 830 is adjusted on scale 904 and the distance "me" 834 is adjusted on scale 905. This insures that if the ear-sidemarker pieces were placed in the patient's external auditory meatuss the arch center 488 in FIG. 5 would coincide with the entry point 827 shown in FIG. 10.

Similarly, the angle "bat" 832 is adjusted on scale 914, distance "at" 829 is adjusted on scale 906 and the distance "mt" 834 is adjusted on scale 908. This insures that if the ear-sidemarker pieces were placed in the patient's external auditory meatuss the tip of the target localizer 56 in FIG. 1 would coincide with the target point 828 shown in FIG. 10. All these positions and angles are frozen on the apparatus by the adjustment screws.

After these adjustments, it is time to determine on the apparatus the line connecting the entry point to the target point. The angle of the pointer support arch 48 about its axis of rotation 486 FIG. 5 and the position of the pointer guide 482 on the arch are manually arranged in such a way that the pointer 482 points precisely toward the tip of the target localizer 56. The pointer support arch 48 and pointer guide 482 are frozen at these positions by their adjustment screws. The pointer 482 is pushed into the pointer guide 482 until the tip of the pointer coincides precisely with the tip of the target localizer 56. The distance "H" 860 along the pointer 484 from the top of the pointer guide 482 to the tip of the target localizer 56 is measured.

Step 3

Figure 13A:
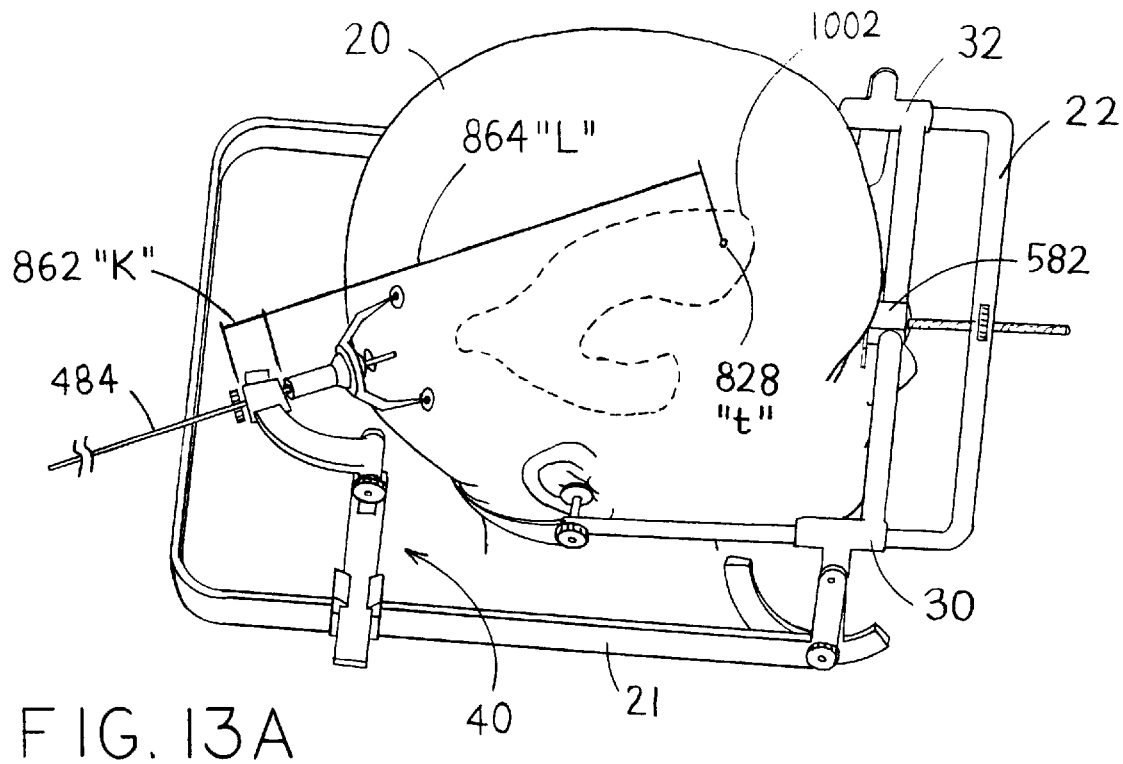
FIGS. 13A–B show the portable guider and the adjustment apparatus installed on patient's head. Top figure A shows the portable guider and the apparatus with the target arm removed attached to the patient's head. Bottom figure B illustrates the use of the portable guider to guide a cathater into the lateral ventricule during surgery.
Figure 13B:
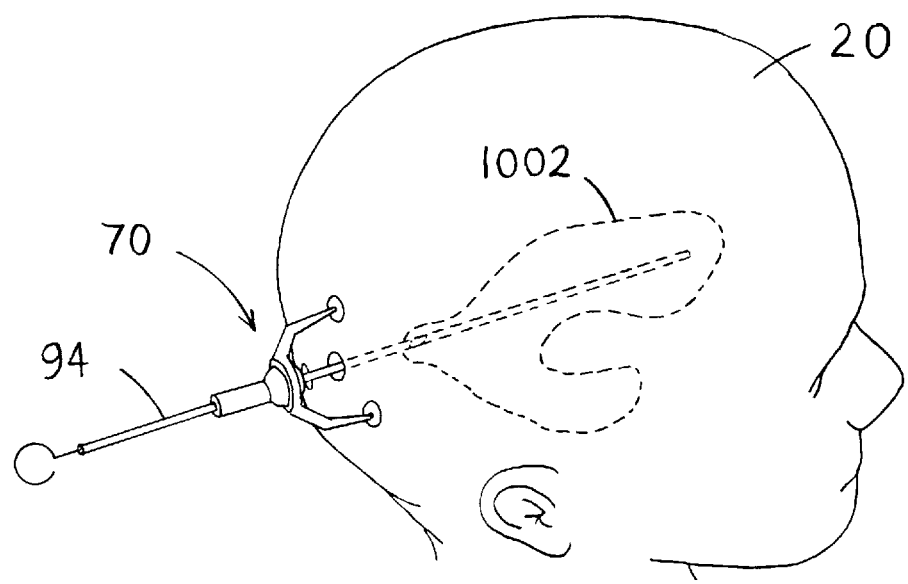

The target assembly 50 is removed from the apparatus by loosening the screw that connects it to the central target arm holder 582 from below FIG. 4. The pointer 484 is taken out of the pointer guide 482. Then the apparatus is installed on the patient's head. The lateral fiducial pieces 23 are pushed toward the external auditory meatuss by turning their screws 232 by equal amounts from both sides until they are tight. The adjustment screw at the front of the secondary frame 22 is turned until the nosepiece 58 sits on the patient's nasion. At this stage the scale 916 must indicate the value of the distance "ab" 831 measured in Step 1. This fact is used by the surgeon as a check on the reliability of his/her progress up to this point. The support bands 28 are fastened around the back of the head. After these operations, the secondary frame 22, the target assembly holders 30,32, and the central target arm holder 582 appear in relation to the patient's head as shown in FIG. 13A. For infant patients, the ear-sidemarker screws for infant 234 which are longer are used.

Step 4

FIG. 13A shows an example of how the main rail frame and guidance assembly 21,40 may appear after the completion of Step 3. As shown in the figure, the portable guider 70 is placed between the guidance assembly 40 and the patient's head. The shaft of the portable guider barrel 72 is aligned with the hole in the pointer guide 482 by inserting the pointer 484 into both the pointer guide and the portable guider barrel. The portable guider is then pushed until it is firmly in contact with the head surface. The portable guider feet 78 are adjusted to be in orientations determined by the surgeon's requirements. At the points of contact of the portable guider feet with the head the portable guider tacks 782 are inserted into the skin. The distance "K" 862 shown in FIG. 13A is measured. This is the distance along the pointer 484 between the pointer guide's 482 top and the top of the portable guider barrel 72. All adjustment screws on the portable guider are tightened.

Due to the preparation of the apparatus described in Step 3, the shaft of the portable guider is now oriented toward the target point 828. The distance "L" 864 between the top of portable guider and the target point equals the distance "H" minus the distance "L", that is, L=H−K.

An important ingredient of the present invention appears clearly at this stage: The results of all of the foregoing measurements and adjustments have been entirely transferred to the portable guider 70. This implies that if the portable guider is removed and reinstalled at the same location on the head, the shaft of the portable guider will continue to point toward the target point 828. Furthermore the distance between the top of the portable guider barrel and the target has the known value L 864, e.g. FIG. 13.

The system is removed from the patient's head before surgery. This leaves the surgeon entirely free of any obstructions which are generally present when other stereotactic frames are used.

Step 5

During surgery, a portable guider barrel 72 with the required bore is chosen based on the surgical instrument that is to be inserted. This is screwed into the portable guider sphere 74. The portable guider is placed in its position on the patient's head by snapping the portable guider feet 78 into the corresponding portable guider tacks 782. When the surgical instrument is inserted into the portable guider barrel's shaft to the depth equaling the value L see Step 4, the tip of the instrument coincides with the target point. A visual example of this step is given in FIG. 13B.

Figure 14A:
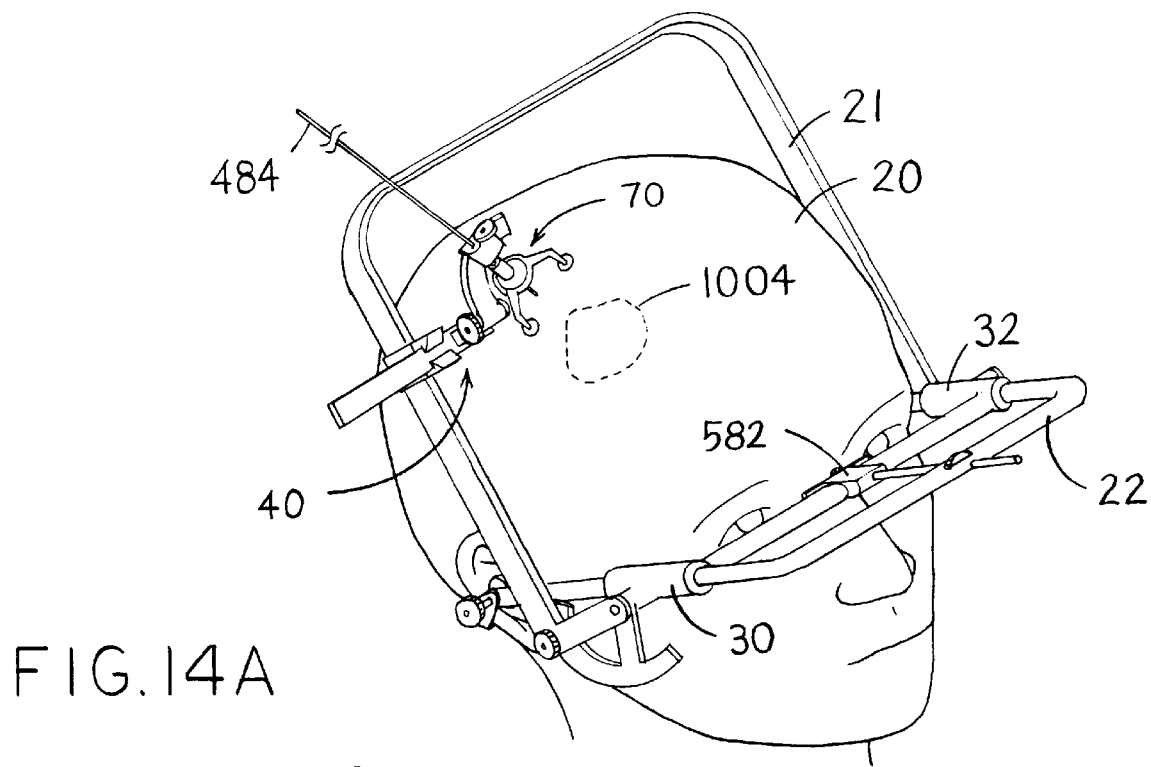
FIGS. 14A–B show the portable guider and the adjustment apparatus installed on patient's head. Top figure A shows the portable guider and the apparatus with the target arm removed attached to the patient's head. Bottom figure B illustrates the use of the portable guider to guide a biopsy forceps to the intracranial lesion.
Figure 14B:
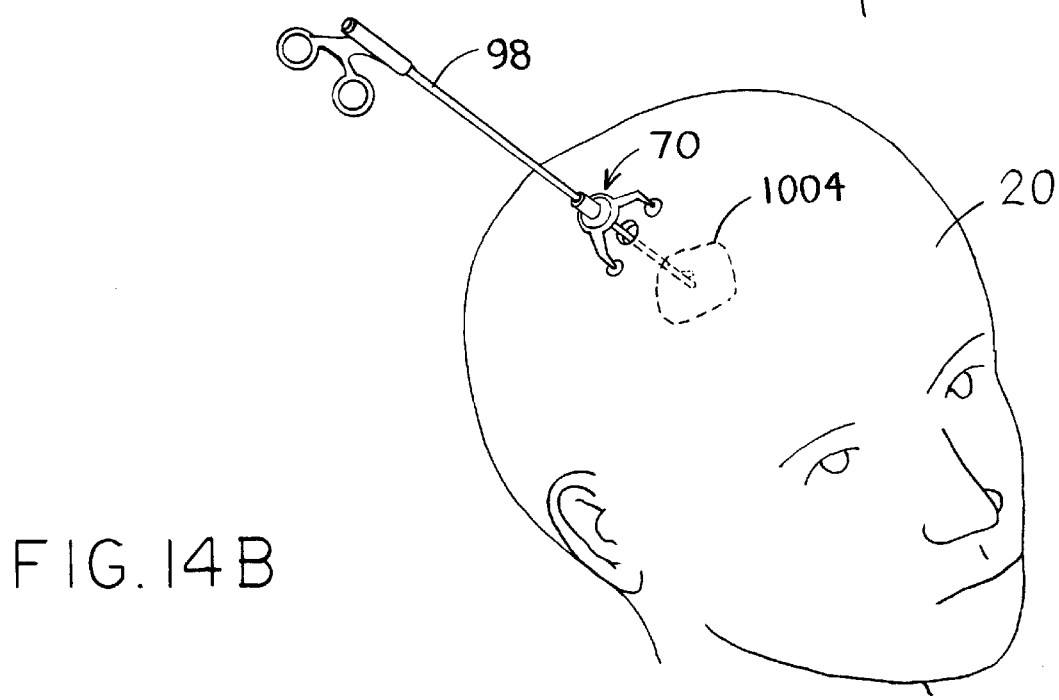

Another visual example of the Steps 4 and 5 is presented in FIG. 14A and B. As an extension of the fact that the invention is able to locate a point on the surface of the head, it can be used to mark an entire curve by using the principles described above. A visual example of the latter is presented in FIG. 15.

Operation with Markers

An important advantage of the present invention is its ability to use the standard output of CT/MRI without the time-consuming need for taking images with markers attached to the patient's head. However, the surgeon may prefer to use the device with markers rather than the natural reference points (external auditory meatus and nasion). In order to do so, an CT/MRI output is obtained showing lateral fiducials and anterior fiducial on the patient's head as shown in FIG. 8.

Figure 8:
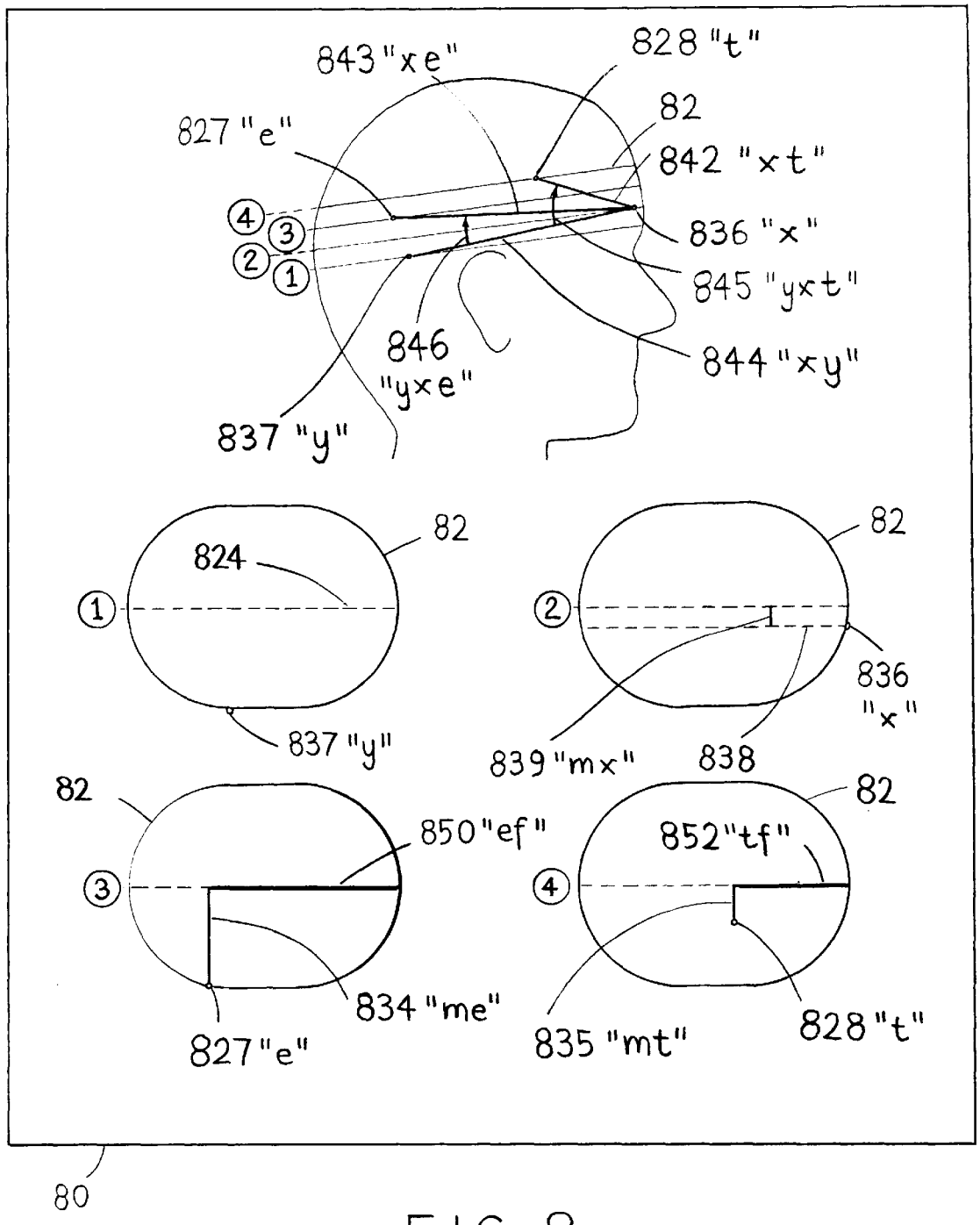
FIG. 8 represents the standard output obtained from CT/MRI along with the distances and angles measured by the surgeon prior to employing the guidance system—markers have been applied before taking the CT/MRI and they serve as reference location indicators.

The measurements that are needed in this case for Step 1 are shown in FIG. 8. They are identical to those shown in FIG. 7 if the points "x" 836 and "y" 837 are substituted for "a" 825 and "b" 826. In this case the anterior fiducial 836 may appear in a position different than the front end of the slice on which it is found. To offset this difference the distance "mx" 839 is measured FIG. 8 as an additional part of Step 1. As the apparatus is adjusted in Step 2, the nose piece 58 is displaced sideways by the amount "mx" scale 918 in FIG. 12 and fixed in this position. No other actions in addition to those described above are required for operating the invention with markers.

Although the invention herein disclosed is calculated to fulfill the objects previously stated it will be obvious that numerous modifications and changes may be devised by those skilled in the art and the appended claims are intended to cover all such modifications and changes within the scope and spirit of the present invention.

We claim:

1. A method for inserting a neurosurgical instrument in a brain of a human patient comprising the steps of substantially sequentially
    (a) identifying a plurality of points on and in a head of the human patient;
    (b) gathering data from a plurality of standard radiological images of the head of the human patient;
    (c) using a plurality of anatomical landmark or artifical markers attached prior to an imaging study so as to determine coordinates of said points;
    (d) preparing an adjusting means by using said coordinates;
    (e) removably and noninvasively installing the adjusting means on said anatomical landmarks or artifical markers;
    (f) preparing an adjustable means for guiding by using the adjusting means, removing the adjusting means, and removably installing only the adjustable means for guiding on the head of the human patient;
    (g) inserting the neurosurgical instrument through the adjustable means for guiding;

whereby a surgeon is able to perform surgery by using only the adjustable means for guiding so that the the adjustable means for guiding may be removed and reinstalled during surgery without losing its function.

2. An apparatus for inserting a neurosurgical instrument in a brain of a human patient comprising a rigid U-shaped member having approximately L-shaped extensions at both ends;

a guidance assembly slidably affixed to said approximately U-shaped member having approximately L-shaped extensions at both ends;

a rigid approximately U-shaped member which can be removably fixed on a head of a human patient and which is slidably affixed to said rigid approximately U-shaped member having approximately L-shaped extensions at both ends;

a target assembly slidably and rotatably affixed to said rigid approximately U-shaped member which can be removably fixed on a head of a human patient;

a portable guider comprising components whose lengths and relative orientations are adjustable.

* * * * *